US011747490B2

(12) United States Patent
Ushikura et al.

(10) Patent No.: US 11,747,490 B2
(45) Date of Patent: Sep. 5, 2023

(54) RADIATION DETECTOR AND RADIOGRAPHIC IMAGING APPARATUS

(71) Applicant: FUJIFILM CORPORATION, Tokyo (JP)

(72) Inventors: Shinichi Ushikura, Kanagawa (JP); Tatsunori Tanimoto, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 365 days.

(21) Appl. No.: 17/497,991

(22) Filed: Oct. 11, 2021

(65) Prior Publication Data

US 2022/0082714 A1    Mar. 17, 2022

Related U.S. Application Data

(63) Continuation of application No. PCT/JP2020/017770, filed on Apr. 24, 2020.

(30) Foreign Application Priority Data

Apr. 26, 2019    (JP) ................. 2019-086596

(51) Int. Cl.
*G01T 1/20* (2006.01)
*A61B 6/00* (2006.01)
*G01T 1/202* (2006.01)

(52) U.S. Cl.
CPC .......... *G01T 1/2018* (2013.01); *A61B 6/4208* (2013.01); *G01T 1/202* (2013.01)

(58) Field of Classification Search
None
See application file for complete search history.

(56) References Cited

U.S. PATENT DOCUMENTS 6,897,449 B1    5/2005 Hata
2004/0211911 A1    10/2004 Hata
(Continued)

FOREIGN PATENT DOCUMENTS

JP    H11-284909 A    10/1999
JP    2008-212343 A    9/2008
(Continued)

OTHER PUBLICATIONS

English language translation of the following: Office action dated Jul. 26, 2022 from the JPO in a Japanese patent application No. 2021-516277 corresponding to the instant patent application.
(Continued)

*Primary Examiner* — Edwin C Gunberg
(74) *Attorney, Agent, or Firm* — SOLARIS Intellectual Property Group, PLLC

(57) ABSTRACT

A radiation detector includes a sensor substrate in which a plurality of pixels for accumulating electric charges generated in response to light converted from radiation is formed in a pixel region of a flexible base material; a conversion layer that is provided on a first surface provided with the pixel region of the base material and converts the radiation into light; an absorption layer that is provided on a side opposite to a side to which the radiation is radiated in a laminate in which the sensor substrate and the conversion layer are laminated and absorbs influence of irregularities generated on the conversion layer on the sensor substrate; and a rigid plate that is provided on a side of the absorption layer opposite to a side facing the laminate and has a higher stiffness than the sensor substrate. Provided are a radiation detector and a radiographic imaging apparatus capable of improving the quality of a radiographic image.

11 Claims, 10 Drawing Sheets

(56) References Cited

U.S. PATENT DOCUMENTS

| | | | |
|---|---|---|---|
| 2009/0014659 A1 | 1/2009 | Hennessy et al. | |
| 2013/0077764 A1 | 3/2013 | Noguchi et al. | |
| 2013/0264461 A1 | 10/2013 | Okada et al. | |
| 2016/0169714 A1 | 6/2016 | Maclaughlin | |
| 2018/0132806 A1 | 5/2018 | Choi et al. | |

FOREIGN PATENT DOCUMENTS

| | | | | |
|---|---|---|---|---|
| JP | 2012-128091 A | | 7/2012 | |
| JP | 2012128091 A | * | 7/2012 | |
| JP | 2013-217769 A | | 10/2013 | |
| JP | 2014-006233 A | | 1/2014 | |
| JP | 2014006233 A | * | 1/2014 | |

OTHER PUBLICATIONS

International Search Report issued in International Application No. PCT/JP2020/017770 dated Jul. 14, 2020.
Written Opinion of the ISA issued in International Application No. PCT/JP2020/017770 dated Jul. 14, 2020.
Extended European Search Report dated Apr. 29, 2022, issued in corresponding EP Patent Application No. 20794058.6.

* cited by examiner

RADIATION DETECTOR AND RADIOGRAPHIC IMAGING APPARATUS

CROSS-REFERENCE TO RELATED APPLICATION

This application is a continuation application of International Application No. PCT/JP2020/017770, filed Apr. 24, 2020, the disclosure of which is incorporated herein by reference in its entirety. Further, this application claims priority from Japanese Patent Application No. 2019-086596 filed on Apr. 26, 2019, the disclosure of which is incorporated herein by reference in its entirety.

BACKGROUND

1. Technical Field

The present disclosure relates to a radiation detector and a radiographic imaging apparatus.

2. Description of the Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses. As this radiation detector, there is one comprising a conversion layer, such as a scintillator, which converts radiation into light, and a sensor substrate in which a plurality of pixels, which accumulate electric charges generated in response to light converted in the conversion layer, are provided in a pixel region of a base material. As a base material of a sensor substrate of such a radiation detector, one using a flexible base material is known (for example, refer to JP2013-217769A). By using the flexible base material, for example, the weight of the radiographic imaging apparatuses (radiation detector) can be reduced, and a subject may be easily imaged.

SUMMARY

There is a case where fine irregularities are generated in a laminate or the like in which the conversion layer is laminated on the sensor substrate. In a case where a load or impact is applied to the radiographic imaging apparatus in the capturing of the radiographic image, there is a case where the irregularities generated in the laminate propagate to the flexible base material, and the quality of the radiographic image generated by the radiation detector deteriorates.

The present disclosure provides a radiation detector and a radiographic imaging apparatus capable of improving the quality of a radiographic image.

A radiation detector according to a first aspect of the present disclosure comprises a sensor substrate in which a plurality of pixels for accumulating electric charges generated in response to light converted from radiation is formed in a pixel region of a flexible base material; a conversion layer that is provided on a surface of the base material provided with the pixel region and converts the radiation into light; and an absorption layer that is provided on a side opposite to a side to which the radiation is radiated in a laminate in which the sensor substrate and the conversion layer are laminated and absorbs influence of irregularities generated on the conversion layer on the sensor substrate; and a rigid plate that is provided on a side of the absorption layer opposite to a side facing the laminate and has a higher stiffness than the sensor substrate.

A radiographic imaging apparatus according to a second aspect of the present disclosure comprises a housing in which the radiation detector of the first aspect is housed in order of the laminate, the absorption layer, and the rigid plate from the side to which the radiation is radiated.

A radiographic imaging apparatus according to a third aspect of the present disclosure is the radiographic imaging apparatus according to the second aspect in which a durometer hardness of the absorption layer is smaller than a durometer hardness of the entire laminate.

A radiographic imaging apparatus according to a fourth aspect of the present disclosure is the radiographic imaging apparatus according to any one of the second to third aspects in which the absorption layer has a surface resistance value of $10^{13} \Omega$ or less.

A radiographic imaging apparatus according to a fifth aspect of the present disclosure is the radiographic imaging apparatus according to any one of the second to fourth aspects, further comprising a reinforcing substrate that is provided between the absorption layer and the laminate and that disperses a compressive force applied to the absorption layer in an in-plane direction of the absorption layer.

A radiographic imaging apparatus according to a sixth aspect of the present disclosure is the radiographic imaging apparatus according to any one of the second to fourth aspects further comprising a reinforcing substrate that is provided on a side of the laminate opposite to the absorption layer side and that disperses a compressive force applied to the absorption layer in an in-plane direction of the absorption layer.

A radiographic imaging apparatus of a seventh aspect of the present disclosure is the radiographic imaging apparatus of the fifth aspect or sixth aspect in which the reinforcing substrate has a bending elastic modulus of 150 MPa or more and 2,500 MPa or less.

A radiographic imaging apparatus according to an eighth aspect of the present disclosure is the radiographic imaging apparatus according to any one of the fifth to seventh aspects in which the reinforcing substrate has a bending stiffness of 540 Pacm$^4$ or more and 140,000 Pacm$^4$ or less.

A radiographic imaging apparatus according to a ninth aspect of the present disclosure is the radiographic imaging apparatus according to any one of the second to eighth aspects further comprising a radiation-shielding layer shielding the radiation and provided between the absorption layer and the rigid plate.

A radiographic imaging apparatus according to a tenth aspect of the present disclosure is the radiographic imaging apparatus according to any one of the second to ninth aspects in which the rigid plate is a plate having carbon as a material.

A radiographic imaging apparatus according to an eleventh aspect of the present disclosure is the radiographic imaging apparatus according to any one of the second to tenth aspects in which further comprising a buffer member that is provided on a side of the laminate on which the radiation is incident.

A radiographic imaging apparatus according to a twelfth aspect of the present disclosure is the radiographic imaging apparatus according to any one of the second to eleventh aspects in which the conversion layer contains columnar crystals of CsI.

A radiographic imaging apparatus according to a thirteenth aspect of the present disclosure is the radiographic imaging apparatus according to any one of the second to twelfth aspects further comprising a control unit that outputs a control signal for reading out electric charges accumulated in the plurality of pixels; a drive unit that reads out the electric charges from the plurality of pixels in accordance with the control signal; and a signal processing unit that receives electrical signals according to the electric charges read from the plurality of pixels and generates image data according to the received electrical signals to output the image data to the control unit.

According to the present disclosure, the quality of a radiographic image can be improved.

BRIEF DESCRIPTION OF THE DRAWINGS

Exemplary embodiments according to the technique of the present disclosure will be described in detail based on the following figures, wherein.

DETAILED DESCRIPTION

Figure 1:
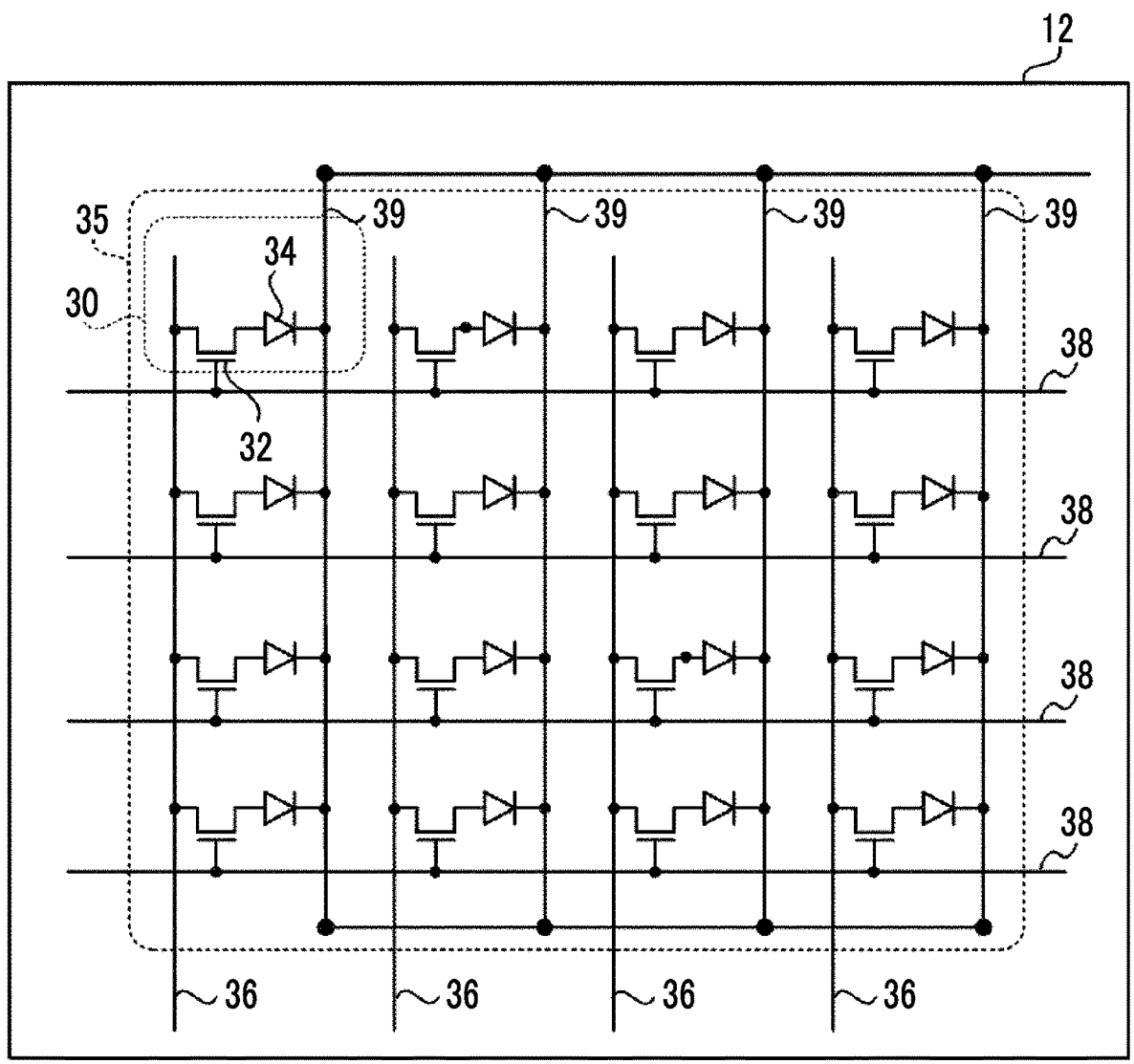
FIG. 1 is a configuration diagram illustrating an example of a configuration of a thin film transistor (TFT) substrate in a radiation detector according to an embodiment.

Hereinafter, embodiments of the present invention will be described in detail with reference to the drawings. In addition, the present embodiments do not limit the present invention.

The radiation detector of the present embodiment has a function of detecting radiation transmitted through a subject to output image information representing a radiographic image of the subject. The radiation detector of the present embodiment comprises a sensor substrate and a conversion layer that converts radiation into light (refer to a sensor substrate 12 and a conversion layer 14 of the radiation detector 10 in FIG. 4).

First, an example of the configuration of the sensor substrate 12 in the radiation detector of the present embodiment will be described with reference to FIG. 1. In addition, the sensor substrate 12 of the present embodiment is a substrate in which a plurality of pixels 30 are formed in a pixel region 35 of the base material 11.

The base material 11 is made of resin and has flexibility. The base material 11 is, for example, a resin sheet containing plastic such as polyimide. The thickness of the base material 11 may be a thickness in which desired flexibility is obtained in accordance with the hardness of the material, the size of the sensor substrate 12, and the like. For example, in a case where the base material 11 is a resin sheet, the thickness thereof may be 5 μm to 125 μm and more preferably 20 μm to 50 μm.

In addition, the base material 11 has characteristics capable of withstanding the manufacture of the pixels 30 to be described in detail below and has characteristics capable of withstanding the manufacture of amorphous silicon thin film transistor (a-Si TFT) in the present embodiment. As such a property of the base material 11, the coefficient of thermal expansion at 300° C. to 400° C. is preferably about the same as that of an amorphous silicon (Si) wafer (for example, ±5 ppm/K), and specifically, preferably 20 ppm/K or less. Additionally, as the percentage of thermal shrinkage of the base material 11, the percentage of thermal shrinkage in a machine direction (MD) at 400° C. in a state where the thickness is 25 μm is preferably 0.5% or less. Additionally, it is preferable that the elastic modulus of the base material 11 does not have a transition point that general polyimide has, in a temperature range of 300° C. to 400° C., and elastic modulus at 500° C. is 1 GPa or more.

Figure 2:
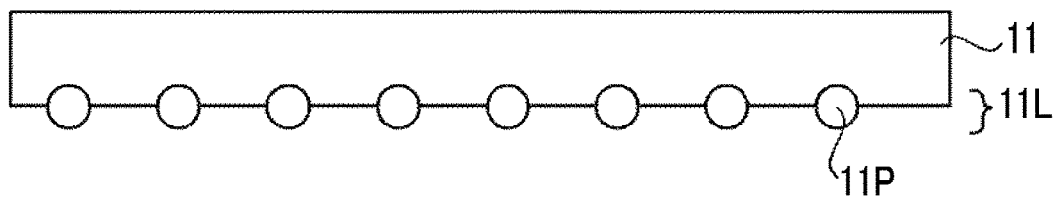
FIG. 2 is a cross-sectional view for explaining an example of a base material of the embodiment.

Additionally, as shown in FIG. 2, it is preferable that the base material 11 of the present embodiment has, on a surface opposite to a side where the conversion layer 14 is provided, a fine particle layer 11L containing inorganic fine particles 11P having an average particle diameter of 0.05 μm or more and 2.5 μm or less, which absorbs backscattered rays caused by itself in order to suppress the backscattered rays. In addition, as the inorganic fine particles 11P, in the case of the resinous base material 11, it is preferable to use an inorganic material of which the atomic number is larger than the atoms constituting the organic material that is the base material 11 and of which the atomic number is 30 or less. Specific examples of such fine particles 11P include $SiO_2$ that is an oxide of Si having an atomic number of 14, MgO that is an oxide of Mg having an atomic number of 12, $Al_2O_3$ that is an oxide of Al having an atomic number of 13, $TiO_2$ that is an oxide of Ti having an atomic number of 22, and the like. A specific example of the resin sheet having such characteristics is XENOMAX (registered trademark).

In addition, the above thicknesses in the present embodiment were measured using a micrometer. The coefficient of thermal expansion was measured according to JIS K7197: 1991. In addition, the measurement was performed by cutting out test pieces from a main surface of the base material 11 while changing the angle by 15 degrees, measuring the coefficient of thermal expansion of each of the cut-out test pieces, and setting the highest value as the coefficient of thermal expansion of the base material 11. The coefficient of thermal expansion is measured at intervals of 10° C. between −50° C. and 450° C. in a machine direction (MD) and a transverse direction (TD), and (ppm/° C.) is converted to (ppm/K). For the measurement of the coefficient of thermal expansion, the TMA4000S apparatus made by MAC Science Co., Ltd. is used, sample length is 10 mm, sample width is 2 mm, initial load is 34.5 g/mm², temperature rising rate is 5° C./min, and the atmosphere is in argon. The elastic modulus was measured according to JIS K7171: 2016. In addition, the measurement was performed by cutting out test pieces from the main surface of the base material 11 while changing the angle by 15 degrees, performing a tensile test for each of the cut-out test pieces, and setting the highest value as the elastic modulus of the base material 11.

Each of the pixels 30 includes a sensor unit 34 that generates and accumulates electric charges in response to the light converted by the conversion layer, and a switching element 32 that reads out the electric charges accumulated by the sensor unit 34. In the present embodiment, as an example, a thin film transistor (TFT) is used as the switching element 32. For that reason, in the following description, the switching element 32 is referred to as a "TFT 32".

The plurality of pixels 30 are two-dimensionally arranged in one direction (a scanning wiring direction corresponding to a transverse direction of FIG. 1, hereinafter referred to as a "row direction"), and a direction intersecting the row direction (a signal wiring direction corresponding to the longitudinal direction of FIG. 1, hereinafter referred as a "column direction") in a pixel region 35 of the sensor substrate 12. Although an array of the pixels 30 is shown in a simplified manner in FIG. 1, for example, 1024×1024 pixels 30 are arranged in the row direction and the column direction.

Additionally, a plurality of scanning wiring lines 38 for controlling switching states (ON and OFF) of the TFTs 32, and a plurality of signal wiring lines 36, which are provided for respective columns of the pixels 30 and from which electric charges accumulated in the sensor units 34 are read out, are provided in a mutually intersecting manner in the radiation detector 10. The plurality of scanning wiring lines 38 are respectively connected to a drive unit 103 (refer to FIG. 5) outside the radiation detector 10 via pads (not shown), respectively, provided in the sensor substrate 12, and thereby, control signals, which are output from the drive unit 103 to control the switching states of the TFTs 32, flow to the plurality of scanning wiring lines 38, respectively. Additionally, the plurality of signal wiring lines 36 are respectively connected to a signal processing unit 104 (refer to FIG. 5) outside the radiation detector 10 via pads (not shown), respectively, provided in the sensor substrate 12, and thereby, electric charges read from the respective pixels 30 are output to the signal processing unit 104.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by connecting the common wiring lines 39 to the bias power source outside the radiation detector 10 via pads (not shown) provided in the sensor substrate 12.

Figure 3:
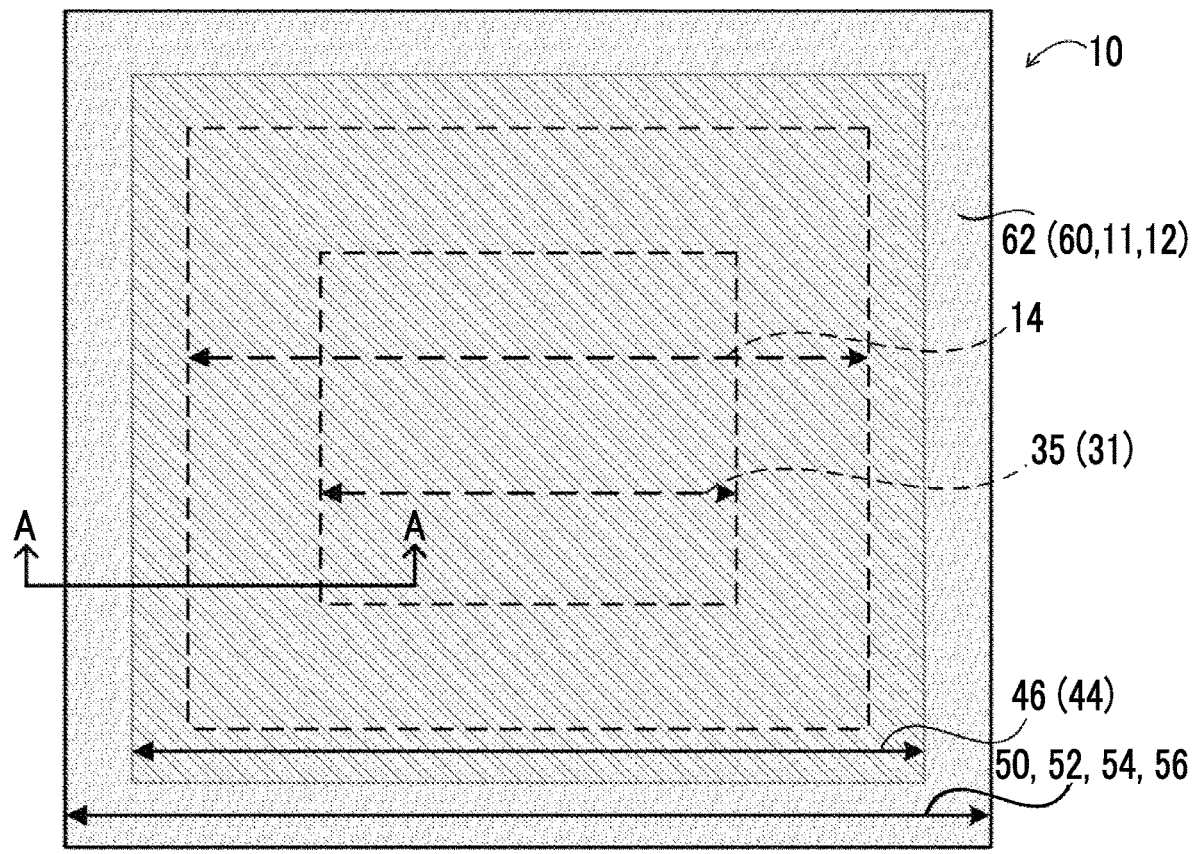
FIG. 3 is a plan view of an example of a penetration side sampling (PSS) type radiation detector of the embodiment as viewed from a side to which radiation is radiated.
Figure 4:
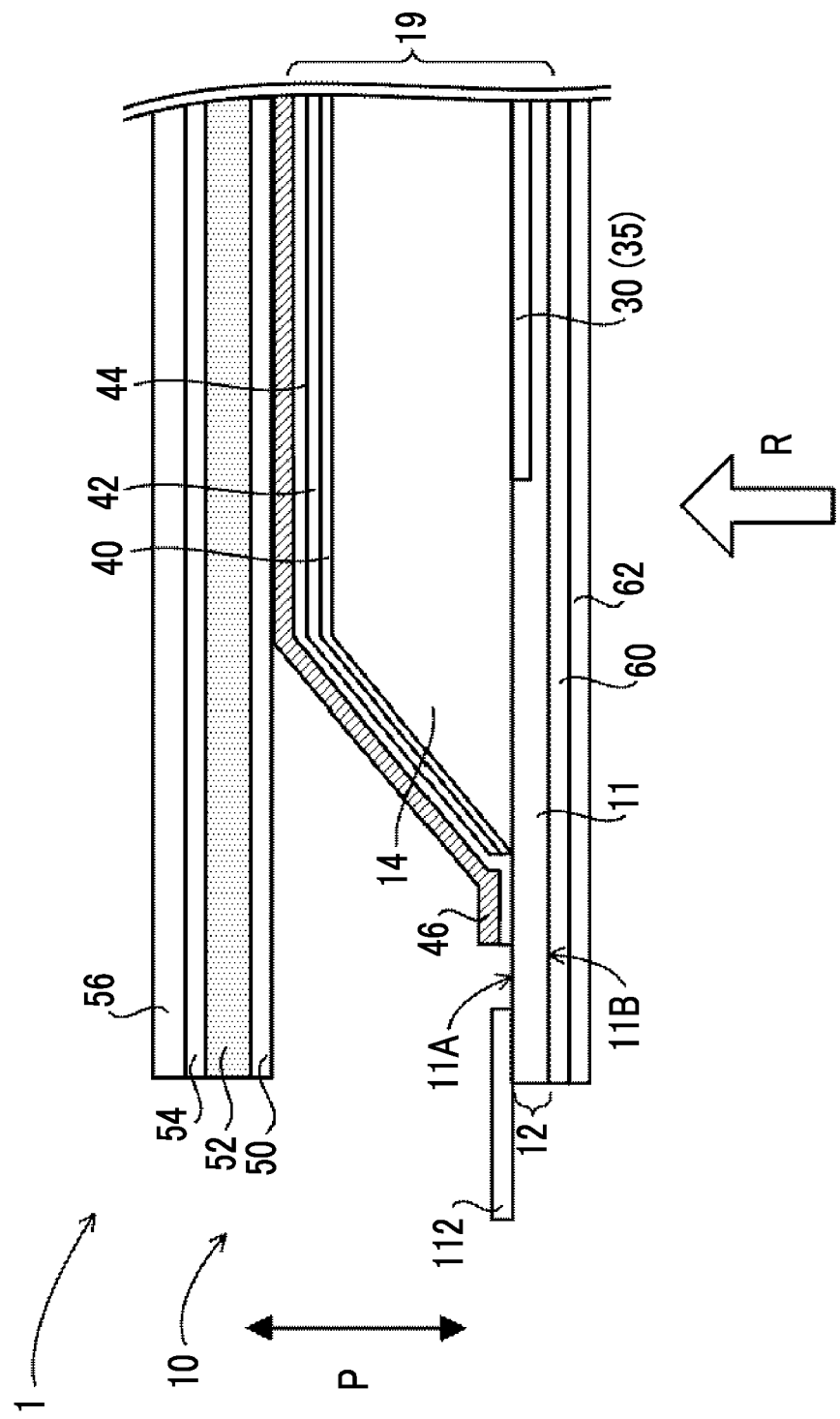
FIG. 4 is a cross-sectional view taken along line A-A of the radiation detector illustrated in FIG. 3.

The radiographic imaging apparatus 1 including the radiation detector 10 of the present embodiment will be described in more detail with reference to FIGS. 3 to 5. The radiation detector 10 of the present embodiment is an irradiation side sampling (ISS) type radiation detector in which a laminate 19 on which the conversion layer 14 is formed is provided on the sensor substrate 12 and radiation R is radiated from the sensor substrate 12 side. FIG. 3 is a plan view of an example of the radiographic imaging apparatus 1 including the radiation detector 10 of the present embodiment as viewed from a side where the sensor substrate 12 is formed. In other words, FIG. 3 is a plan view of the radiographic imaging apparatus 1 (radiation detector 10) as viewed from a side to which the radiation R is radiated. Additionally, FIG. 4 is a cross-sectional view taken along line A-A of an example of the radiation detector 10 in FIG. 3. Moreover, FIG. 5 is a cross-sectional view of an example of the radiographic imaging apparatus 1 in a state where the radiation detectors 10 of FIGS. 3 and 4 are housed in a housing 120.

In the following, here, the term "on" in the structure of the radiation detector 10 means "on" in a positional relationship with reference to the sensor substrate 12 side in FIG. 4. For example, the conversion layer 14 is provided on the sensor substrate 12.

Figure 5:
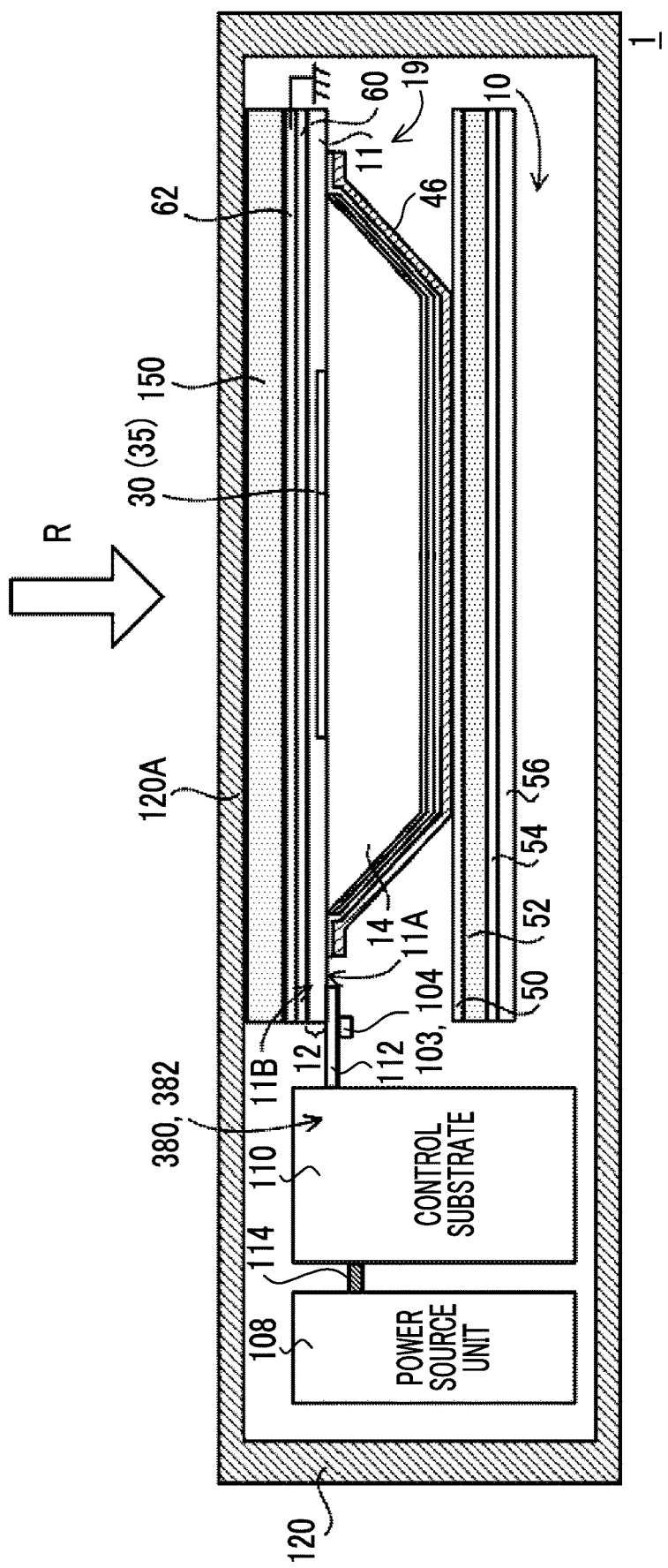
FIG. 5 is a cross-sectional view showing an example of a radiographic imaging apparatus according to the embodiment.

As shown in FIGS. 3 to 5, the radiographic imaging apparatus 1 of the present embodiment includes a protective layer 62, an antistatic layer 60, a sensor substrate 12, the conversion layer 14, a reinforcing substrate 50, an absorption layer 52, and a radiation-shielding layer 54, and a rigid plate 56. Additionally, as shown in FIG. 5, in the radiographic imaging apparatus 1, the protective layer 62, the antistatic layer 60, the sensor substrate 12, the conversion layer 14, the reinforcing substrate 50, the absorption layer 52, the radiation-shielding layer 54, and the rigid plate 56 are housed in the housing 120 in this order from the side to which the radiation R is radiated.

As shown in FIGS. 3 to 5, the conversion layer 14 of the present embodiment is provided on a partial region of the sensor substrate 12 including the pixel region 35 on the first surface 11A of the base material 11. In this way, the conversion layer 14 of the present embodiment is not provided on the region of an outer peripheral portion on the first surface 11A of the base material 11.

In the present embodiment, a scintillator including CsI (cesium iodide) is used as an example of the conversion layer 14. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray radiation. In addition, the emission peak wavelength in a visible light region of CsI:Tl is 565 nm.

In the radiation detector 10 of the present embodiment, as in the example shown in FIG. 4, the conversion layer 14 is directly formed on the sensor substrate 12 as strip-shaped columnar crystals (not shown) by vapor-phase deposition methods, such as a vacuum vapor deposition method, a sputtering method, and a chemical vapor deposition (CVD) method. For example, in a case where CsI:Tl is used as the conversion layer 14, a vacuum vapor deposition method is used as a method of forming the conversion layer 14. In the vacuum vapor deposition method, CsI:Tl is heated and gasified by heating means, such as a resistance heating-type crucible in an environment with a vacuum degree of 0.01 Pa to 10 Pa, and CsI:Tl is deposited on the sensor substrate 12 with the temperature of the sensor substrate 12 as the room temperature (20° C.) to 300° C. As the thickness of the conversion layer 14, 100 μm to 800 μm is preferable.

In addition, in the present embodiment, end parts of columnar crystals of the conversion layer 14 on a base point side (the sensor substrate 12 side in the present embodiment) in a growth direction are referred to as "roots", and sharpened end parts opposite to the roots in the growth direction are referred to as "tips". In addition, it is preferable that a buffer layer (not shown) is provided between the sensor substrate 12 and the conversion layer 14. As the buffer layer in this case, a polyimide (PI) film or a parylene (registered trademark) film is used.

Additionally, as shown in FIGS. 3 and 4, the radiation detector 10 of the present embodiment comprises a pressure-sensitive adhesive layer 40, a reflective layer 42, an adhesive layer 44, and a protective layer 46. In addition, in the following, a direction in which the sensor substrate 12 and the conversion layer 14 are lined up (upward-downward direction in FIG. 4) is referred to as a lamination direction (refer to FIG. 4, a lamination direction P).

In the present embodiment, as an example, as shown in FIG. 4, the pressure-sensitive adhesive layer 40 and the reflective layer 42 are provided on the entire conversion layer 14. Additionally, the pressure-sensitive adhesive layer 40 and the reflective layer 42 are not directly provided on the sensor substrate 12.

The pressure-sensitive adhesive layer 40 of the present embodiment is a light-transmitting layer, and examples of the material of the pressure-sensitive adhesive layer 40 include an acrylic pressure sensitive adhesive, a hot-melt pressure sensitive adhesive, and a silicone adhesive. Examples of the acrylic pressure sensitive adhesive include urethane acrylate, acrylic resin acrylate, epoxy acrylate, and the like. Examples of the hot-melt pressure sensitive adhesive include thermoplastics, such as ethylene-vinyl acetate copolymer resin (EVA), ethylene-acrylate copolymer resin (EAA), ethylene-ethyl acrylate copolymer resin (EEA), and ethylene-methyl methacrylate copolymer (EMMA).

As the thickness X of the pressure-sensitive adhesive layer 40 increases (that is, as the interval between the conversion layer 14 and the reflective layer 42 increases), the light converted by the conversion layer 14 is blurred within the pressure-sensitive adhesive layer 40. Therefore, the radiographic image obtained by the radiation detector 10 becomes a blurred image as a result. For that reason, as the thickness of the pressure-sensitive adhesive layer 40 increases, modulation transfer function (MTF) and detective quantum efficiency (DQE) decreases, and the degree of decrease also increases.

On the other hand, in a case where the thickness of the pressure-sensitive adhesive layer 40 is made too small, including a case where the pressure-sensitive adhesive layer 40 is not provided, there is a case where a minute air layer is formed between the conversion layer 14 and the reflective layer 42. In this case, the multiple reflection of the light directed from the conversion layer 14 to the reflective layer 42 occurs between the air layer and the conversion layer 14 and between the air layer and the reflective layer 42. In a case where the light is attenuated by the multiple reflection, the sensitivity of the radiation detector 10 decreases. In a case where the thickness of the pressure-sensitive adhesive layer 40 exceeds 7 µm, the degree of decrease in DQE becomes larger and is lower than in a case where the thickness of the pressure-sensitive adhesive layer 40 is 0 µm). That is, in a case where the thickness of the pressure-sensitive adhesive layer 40 exceeds 7 µm, the DQE is lower than in a case where the pressure-sensitive adhesive layer 40 is not provided. Additionally, in a case where the thickness of the pressure-sensitive adhesive layer 40 is less than 2 µm, the sensitivity of the radiation detector 10 decreases. Thus, in the present embodiment, the thickness of the pressure-sensitive adhesive layer 40 is set to 2 µm or more and 7 µm or less. In addition, the refractive index of the pressure-sensitive adhesive layer 40 is approximately 1.5, although the refractive index depends on the material.

In addition, the pressure-sensitive adhesive layer 40 has a function of fixing the reflective layer 42 to the conversion layer 14. However, in a case where the thickness of the pressure-sensitive adhesive layer 40 is 2 µm or more, it is possible to obtain a sufficient effect of suppressing the deviation of the reflective layer 42 in an in-plane direction (a direction intersecting the thickness direction) with respect to the conversion layer 14.

Meanwhile, as an example, as shown in FIG. 4, the reflective layer 42 is provided on the pressure-sensitive adhesive layer 40 and covers the entire upper surface of the pressure-sensitive adhesive layer 40 itself. The reflective layer 42 has a function of reflecting the light converted by the conversion layer 14.

As a material of the reflective layer 42, it is preferable to use an organic material, and it is preferable to use, for example, at least one of white polyethylene terephthalate (PET), $TiO_2$, $Al_2O_3$, foamed white PET, a polyester-based high-reflection sheet, specular reflection aluminum, or the like. Particularly, it is preferable to use the white PET as the material from a viewpoint of reflectivity.

In addition, the white PET is obtained by adding a white pigment, such as $TiO_2$ or barium sulfate, to PET. Additionally, the polyester-based high-reflection sheet is a sheet (film) having a multilayer structure in which a plurality of thin polyester sheets are laminated. Additionally, the foamed white PET is a white PET of which the surface is porous.

In the present embodiment, the thickness of the reflective layer 42 is 10 µm or more and 40 µm or less. In a case where the thickness of the reflective layer 42 is increased, there is a case where a level difference between an upper surface of an outer peripheral portion of the reflective layer 42 and an upper surface of the conversion layer 14 increases and at least one of the adhesive layer 44 or the protective layer 46 is lifted. Additionally, in a case where the thickness of the reflective layer 42 increases, a so-called stiffness state is brought about. Therefore, there is a case where bending does not occur easily along the inclination of the peripheral edge part of the conversion layer 14 and is not easily processed. For that reason, from these viewpoints, in the radiation detector 10 of the present embodiment, in a case where the white PET is used as the material of the reflective layer 42, the thickness of the reflective layer 42 is set to 40 µm or less as described above.

On the other hand, as the thickness of the reflective layer 42 decreases, reflectivity decreases. In a case where the reflectivity decreases, the quality of a radiographic image to be obtained by the radiation detector 10 also tends to deteriorate. For that reason, from the viewpoint of the quality of the radiographic image obtained by the radiation detector 10, it is preferable to set the lower limit of the thickness of the reflective layer 42 in consideration of a desired reflectivity (for example, 80%). In the radiation detector 10 of the present embodiment, in a case where the white PET is used as the material of the reflective layer 42, the thickness of the reflective layer 42 is set to 10 µm or more as described above.

Meanwhile, as an example, as shown in FIG. 4, the adhesive layer 44 is provided from above a region in the vicinity of an outer peripheral portion of the conversion layer 14 in the sensor substrate 12 to a region covering an end part of the reflective layer 42. In other words, in the radiation detector 10 of the present embodiment, the adhesive layer 44 that covers the entire conversion layer 14 in which the pressure-sensitive adhesive layer 40 and the reflective layer 42 are provided is directly fixed (adhered) to the surface of the sensor substrate 12. The adhesive layer 44 has a function of fixing the reflective layer 42 to the sensor substrate 12 and the conversion layer 14. Additionally, the adhesive layer 44 has a function of fixing the protective layer 46. Examples of the material of the adhesive layer 44 include the same materials as the pressure-sensitive adhesive layer 40. In addition, in the present embodiment, the adhesive force of the adhesive layer 44 is stronger than the adhesive force of the pressure-sensitive adhesive layer 40.

Moreover, as an example, as shown in FIG. 4, the protective layer 46 is provided on the adhesive layer 44, and the protective layer 46 of the present embodiment covers the entire upper surface of the adhesive layer 44 that covers the conversion layer 14 in a state in which the upper surface thereof is covered with the pressure-sensitive adhesive layer 40 and the reflective layer 42. The protective layer 46 has a function of protecting the conversion layer 14 from moisture, such as humidity. Additionally, the protective layer 46 has a function of fixing the reflective layer 42 to the sensor substrate 12 and the conversion layer 14 together with the adhesive layer 44. Examples of the material of the protective layer 46 include organic films, and specifically include PET, polyphenylene sulfide (PPS), biaxially oriented polypropylene film (OPP), polyethylene naphthalate (PEN), PI, and the like. Additionally, as the protective layer 46, an ALPET (registered trademark) sheet obtained by laminating aluminum, for example by causing aluminum foil to adhere to an insulating sheet (film), such as polyethylene terephthalate may be used.

Additionally, the antistatic layer 60 and the protective layer 62 are provided on the side of the laminate 19 to which the radiation R is radiated, in other words, on a second surface 11B side of the base material 11 in the sensor substrate 12. As shown in FIG. 4, the antistatic layer 60 is provided on the second surface 11B of the base material 11 and has a function of preventing the sensor substrate 12 from being charged. As an example, in the antistatic layer 60 of the present embodiment, a film using an antistatic paint "Colcoat" (product name: manufactured by Colcoat Co., Ltd.) is used as the antistatic layer 60.

The protective layer 62 is provided on the side of the antistatic layer 60 opposite to a side in contact with the base material 11, and has a function of preventing the sensor substrate 12 from being charged, similar to the antistatic layer 60. As an example, in the protective layer 62 of the present embodiment, an Alpet (registered trademark) sheet in which aluminum is laminated by causing an aluminum foil to adhere to an insulating sheet (film) is used as the protective layer 62. Additionally, as shown in FIG. 5, the protective layer 62 is connected to a ground for discharging the electric charges that stay in the antistatic layer 60 and the protective layer 62. In the present embodiment, as an example of the ground, a so-called frame ground in which the housing 120 is connected to the protective layer 62 as a ground is used, but the ground connecting the protective layer 62 is not limited to the present embodiment and may be a part that supplies a constant potential. Additionally, earth may be applied instead of the ground. Additionally, as shown in FIG. 5, in the radiographic imaging apparatus 1 of the present embodiment, the buffer member 150 is provided between the protective layer 62 and the top plate 120A having an irradiation surface to which the radiation R is radiated in the housing 120. The buffer member 150 has a function of absorbing an impact due to a load of a subject applied to the top plate 120A of the housing 120 and absorbing the influence of deflection of the top plate 120A. Additionally, the buffer member 150 of the present embodiment has a function of absorbing irregularities generated in the housing 120A. Examples of the buffer member 150 include a material having a Shore E hardness, which is a durometer hardness, similar to the absorption layer 52 described below.

In addition, the protective layer 62 is not limited to a layer having an antistatic function, and may have at least one of a moistureproof function or an antistatic function for the pixel region 35. In addition to the Alpet (registered trademark) sheet of the present embodiment, a parylene (registered trademark) film, an insulating sheet such as PET, or the like can be used as the protective layer.

Moreover, the reinforcing substrate 50, the absorption layer 52, the radiation-shielding layer 54, and the rigid plate 56 are provided on the side of the laminate 19 opposite to the side to which the radiation R is radiated, in other words, on the side of the conversion layer 14 opposite to the side in contact with the sensor substrate 12. The reinforcing substrate 50, the absorption layer 52, the radiation-shielding layer 54, and the rigid plate 56 are laminated on the conversion layer 14 in this order.

The absorption layer 52 has a function of absorbing the irregularities generated in the conversion layer 14 of the laminate 19 due to the irregularities of the laminate 19 of the radiation detector 10, the housing 120, or the like, thereby suppressing the propagation of the irregularities to the sensor substrate 12.

Figure 11:
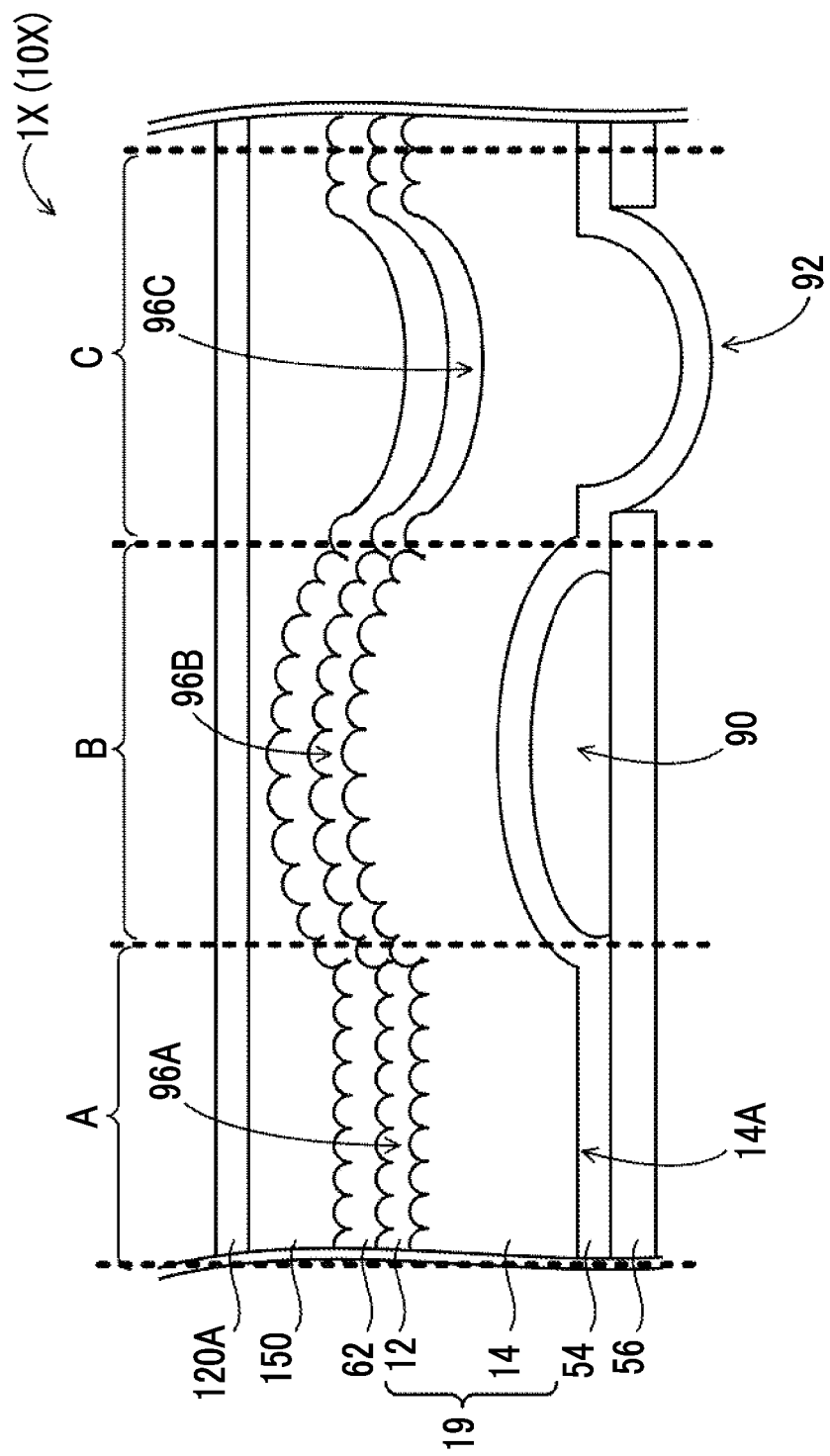
FIG. 11 is a cross-sectional view for explaining the influence of irregularities generated on a conversion layer on a sensor substrate in an example of a radiation detector (radiographic imaging apparatus) of a comparative example.

First, the irregularities generated in the laminate 19 due to the irregularities of the laminate 19 itself, the housing 120, or the like will be described with reference to FIG. 11. FIG. 11 shows a radiation detector 10X (radiographic imaging apparatus 1X) in a state where the reinforcing substrate 50 and the absorption layer 52 are not provided, unlike the radiation detector 10 of the present embodiment.

A region A of FIG. 11 is an example of a region including irregularities 96A caused by the conversion layer 14. As described above, the conversion layer 14 is formed as columnar crystals 14A on the sensor substrate 12. In this case, the radiation-shielding layer 54 side of the conversion layer 14 is tips of the columnar crystals 14A. However, since the base material 11 of the sensor substrate 12 is relatively soft and easily deflected as described above, as shown in the region A of FIG. 11, there is a case where the irregularities of the tips of the columnar crystals 14A are propagated to the sensor substrate 12 side, and the irregularities 96A are generated not on the distal end side of the conversion layer 14 but on the sensor substrate 12 on the root side. So to speak, there is a case where the irregularities of the columnar crystals 14A of the conversion layer 14 are transferred to the sensor substrate 12 on the root side.

Additionally, the region B of FIG. 11 is an example of a region including irregularities 96B caused by bubbles 90 generated in the radiation-shielding layer 54. There is a case where irregularities are generated between the radiation-shielding layer 54 and the rigid plate 56 due to the bubbles 90 generated in the radiation-shielding layer 54. Mainly, as shown in the region B of FIG. 11, there is a case where the radiation-shielding layer 54 enters the conversion layer 14 side and the irregularities are generated in the conversion layer 14. In this case, there is a case where the influence of the irregularities generated by the radiation-shielding layer 54 is propagated, so that the irregularities 96B are generated in the sensor substrate 12.

Additionally, a region C of FIG. 11 is an example of a region including irregularities 96C caused by the irregularities 92 of the rigid plate 56. There is a case where fine irregularities are generated in the surface of the rigid plate 56. For example, an example of a state where the irregularities 92 in the region C of FIG. 11 are irregularities due to the recesses of the rigid plate 56 and the irregularities are generated in the laminate 19 due to the irregularities 92 of the rigid plate 56 is shown. As shown in the region C of FIG. 11, there is a case where the irregularities are generated in the radiation-shielding layer 54 due to the irregularities 92 of the rigid plate 56 and the irregularities 96C are generated in the sensor substrate 12 as the influence of the irregularities generated due to the rigid plate 56 propagate.

In this way, as shown in FIG. 11, the base material 11 of the sensor substrate 12 is relatively easily deflected. Therefore, for example, in a case where t may be softer than the other layers (members) forming the radiation detector 10X, there is a case where the influence of irregularities caused by the radiographic imaging apparatus 1X such as the laminate 19 or the housing 120 are propagated and the irregularities are generated in the sensor substrate 12. In particular, in a case where pressure, impact, or the like is applied to the top plate 120A of the housing 120, such as in a case where a load of the subject is applied, the influence of the irregularities are likely to propagate to the sensor substrate 12, and the irregularities are likely to be generated in the sensor substrate 12. There is a case where the irregularities generated in the sensor substrate 12 appear as image unevenness in a radiographic image obtained by the radiation detector 10X.

In contrast, the absorption layer 52 of the present embodiment is provided on the side of the laminate 19 opposite to the side where the radiation R is radiated, and in the radiation detector 10 of the present embodiment, on the conversion layer 14 as shown in FIGS. 3 to 5. As described above, the absorption layer 52 has a function of absorbing the influence of the irregularities caused by the laminate 19, the housing 120, or the like and suppressing the influence of the irregularities from being propagated to the sensor substrate 12.

The absorption layer 52 is a layer made of a soft material for absorbing the influence of the irregularities and has a durometer hardness smaller than the durometer hardness of the entire laminate 19. In addition, a hardness measuring method in the present embodiment is obtained by setting a sample in a type E durometer conforming to JIS K6253 and performing a measurement 15 seconds after the contact of a push needle.

Specific materials for the absorption layer 52 include foams such as urethane foam, polyethylene, rubber sponge, and silicon foam, urethane gel, and the like.

Figure 6:
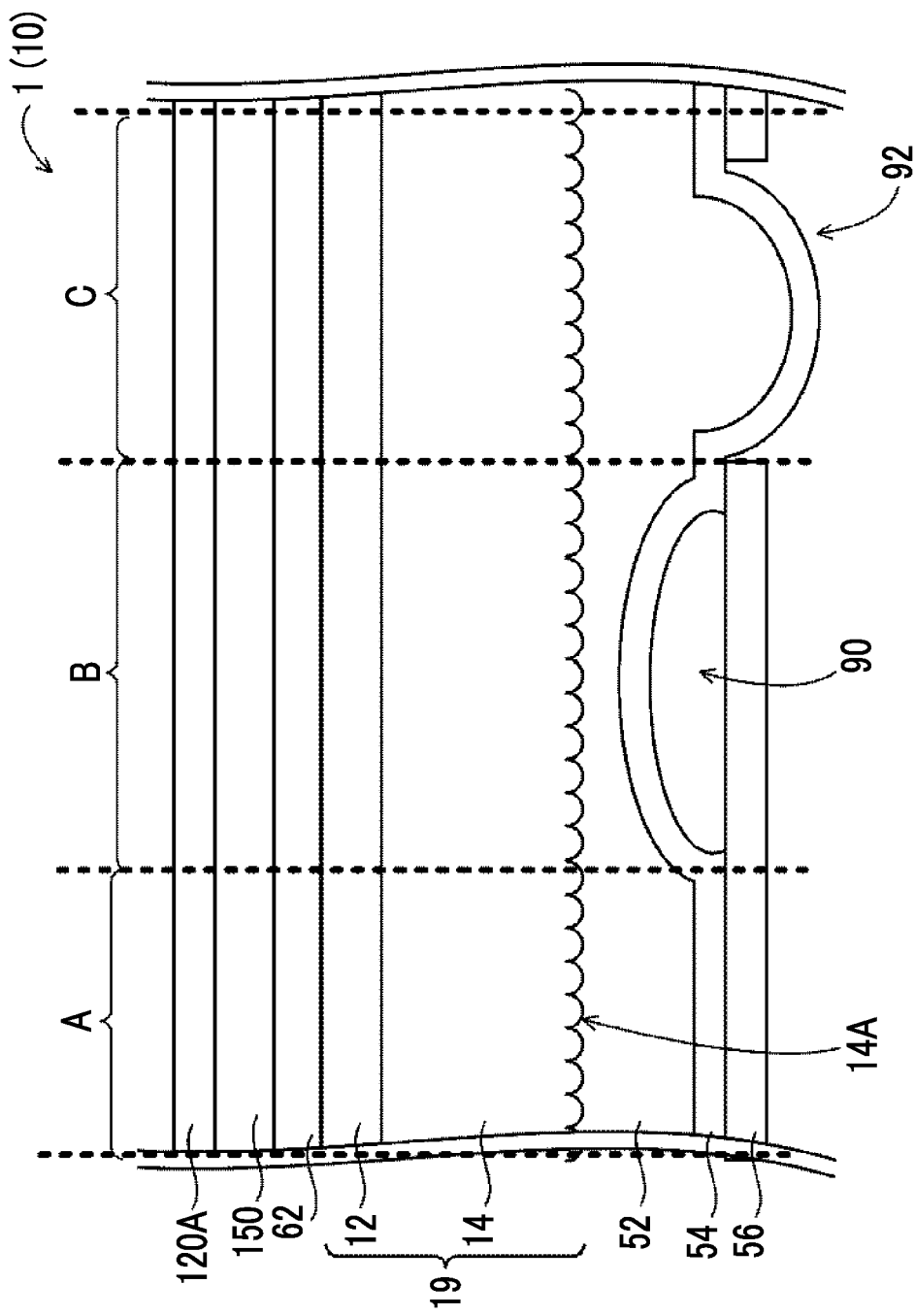
FIG. 6 is a cross-sectional view for explaining the action of an absorption layer in the radiation detector of the embodiment.

In the radiographic imaging apparatus 1 (radiation detector 10) of the present embodiment, as shown in FIG. 6, by providing the absorption layer 52, the absorption layer 52 is deformed in accordance with the irregularities of the columnar crystal 14A even in the region A including the irregularities of the columnar crystals 14A of the conversion layer 14. Accordingly, the irregularities are not propagated to the sensor substrate 12.

Additionally, as shown in FIG. 6, by providing the absorption layer 52, the absorption layer 52 is deformed in accordance with the bubbles 90 even in the region B where the bubbles 90 are generated by the radiation-shielding layer 54. Accordingly, the irregularities caused by the bubbles 90 are not propagated to the sensor substrate 12.

Moreover, as shown in FIG. 6, by providing the absorption layer 52, the absorption layer 52 is deformed in accordance with the irregularities 92 even in the region C where the irregularities 92 of the rigid plate 56 are generated. Accordingly, the irregularities caused by the irregularities 92 are not propagated to the sensor substrate 12.

In this way, according to the radiation detector 10 of the present embodiment, the absorption layer 52 has the shape according to the irregularities generated in the conversion layer 14 of the laminate 19 due to the irregularities of the laminate 19 of the radiation detector 10, the housing 120, or the like. Therefore, the propagation of the irregularities to the sensor substrate 12 can be suppressed.

As shown in FIGS. 3 to 5, the absorption layer 52 of the present embodiment has the same size (area) as the first surface 11A side of the base material 11 in the sensor substrate 12. The size of the absorption layer 52 is not limited to the form shown in FIGS. 3 to 5 but is preferably larger than that of the sensor substrate 12 and preferably has at least an area larger than that of the conversion layer 14.

The thickness of the absorption layer 52 (the thickness in the lamination direction P) is determined in accordance with a size assumed as the size of the irregularities caused by the laminate 19 or the housing 120, for example, the bubbles 90 or the irregularities 92 shown in FIG. 5. The absorption layer 52 preferably has at least a thickness larger than the size of the bubbles 90 or the irregularities 92.

In addition, the absorption layer 52 preferably has an antistatic function for preventing the sensor substrate 12 from being charged, or has conductivity, and preferably has a surface resistance value of $10^{13}\Omega$ or less. As the absorption layer 52 having conductivity, for example, a material in which conductive carbon is kneaded into a polyethylene resin can be applied.

Additionally, the reinforcing substrate 50 has a function of dispersing a compressive force applied to the absorption layer 52 in an in-plane direction of the absorption layer 52, and disperses the compressive force applied to the absorption layer 52, thereby uniformly compressing the absorption layer 52.

The reinforcing substrate 50 preferably uses a material having a bending elastic modulus of 150 MPa or more and 2,500 MPa or less. A method of measuring the bending elastic modulus is based on, for example, JIS K 7171:2016 Standard. The reinforcing substrate 50 preferably has a higher bending stiffness than the base material 11 from the viewpoint of dispersing the compressive force applied to the absorption layer 52 in the in-plane direction of the absorption layer 52. In addition, in a case where the bending elastic modulus becomes low, the bending stiffness also becomes low. In order to obtain a desired bending stiffness, the thickness of the reinforcing substrate 50 should be made large, and the thickness of the entire radiation detector 10 increases. Considering the material of the reinforcing substrate 50, the thickness of the reinforcing substrate 50 tends to be relatively large in a case where a bending stiffness exceeding 140,000 Pacm$^4$ is to be obtained. For that reason, in view of obtaining appropriate stiffness and considering the thickness of the entire radiation detector 10, the material used for the reinforcing substrate 50 preferably has a bending elastic modulus of 150 MPa or more and 2,500 MPa or less. Additionally, the bending stiffness of the reinforcing substrate 50 is preferably 540 Pacm$^4$ or more and 140,000 Pacm$^4$ or less.

The reinforcing substrate 50 of the present embodiment is a substrate having plastic as a material. In a case where the plastic used as the material for the reinforcing substrate 50 is preferably a thermoplastic resin, and include at least one of polycarbonate (PC), PET, styrol, acrylic, polyacetase, nylon, polypropylene, acrylonitrile butadiene styrene (ABS), engineering plastics, or polyphenylene ether. In addition, the reinforcing substrate 50 is more preferably at least one of polypropylene, ABS, engineering plastics, PET, or polyphenylene ether among these, is more preferably at least one of styrol, acrylics, polyacetase, or nylon, and is more preferably at least one of PC or PET.

Additionally, the radiation-shielding layer 54 provided on the reinforcing substrate 50 has a function of shielding the radiation R transmitted through the laminate 19 and suppressing the radiation R transmitted to the outside of the housing 120. Examples of the radiation-shielding layer 54 include a plate such as lead.

Moreover, the rigid plate 56 provided on the radiation-shielding layer 54 supports the radiation detector 10. The rigid plate 56 has a higher stiffness than the sensor substrate 12, and for example, carbon or the like is used.

The housing 120 shown in FIG. 5, which houses the radiation detector 10 of the present embodiment, is preferably lightweight, has a low absorbance of radiation R, particularly X-rays, and has a high stiffness, and is preferably made of a material having a sufficiently high elastic modulus. As the material of the housing 120, it is preferable to use a material having a bending elastic modulus of 10,000 MPa or more. As the material of the housing 120, carbon or carbon fiber reinforced plastics (CFRP) having a bending elastic modulus of about 20,000 to 60,000 MPa can be suitably used.

In the capturing of a radiographic image by the radiographic imaging apparatus 1, a load from a subject is applied to the top plate 120A of the housing 120. In a case where the stiffness of the housing 120 is insufficient, there are concerns that problems may occur such that the sensor substrate 12 is deflected due to the load from the subject and the pixels 30 are damaged. By accommodating the radiation detector 10 inside the housing 120 consisting of a material having a bending elastic modulus of 10,000 MPa or more, it is possible to suppress the deflection of the sensor substrate 12 due to the load from the subject.

As shown in FIG. 5, the radiation detector 10, the power source unit 108, and a control substrate 110 are provided side by side in a direction intersecting an incidence direction of radiation R within the housing 120.

The control substrate 110 is a substrate in which an image memory 380 for storing image data according to the electric charges read from the pixels 30 of the sensor substrate 12, a control unit 382 for controlling reading or the like of the electric charges from the pixels 30, and the like are formed, and is electrically connected to the pixels 30 of the sensor substrate 12 by a flexible cable 112 including a plurality of signal wiring lines. In addition, in the radiographic imaging apparatus 1 illustrated in FIG. 5 the control substrate 110 is a so-called chip on film (COF) in which a drive unit 103 for controlling the switching states of the TFTs 32 of the pixels 30 under the control of the control unit 382, and a signal processing unit 104 for creating and outputting image data according to the electric charges read from the pixels 30 are provided on the flexible cable 112. However, at least one of the drive unit 103 or the signal processing unit 104 may be formed in the control substrate 110.

Additionally, the control substrate 110 is connected to the power source unit 108, which supplies electrical power to the image memory 380, the control unit 382, and the like that are formed in the control substrate 110, by a power source line 114.

Figure 7:
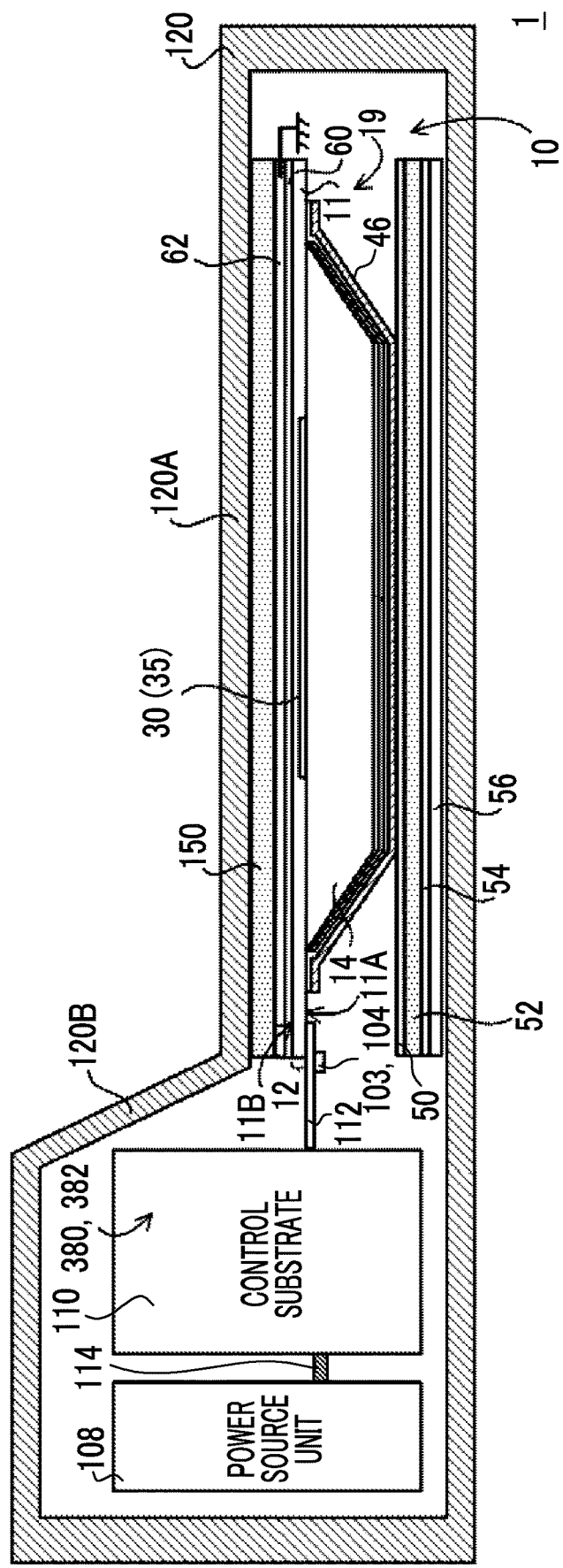
FIG. 7 is a cross-sectional view showing another example of the radiographic imaging apparatus of the embodiment.

In addition, as shown in FIG. 5, there are many cases where each of the power source unit 108 and the control substrate 110 is thicker than the radiation detector 10. In such a case, as in the example shown in FIG. 7, the thickness of the portion of the housing 120 in which the radiation detector 10 is provided may be smaller than the thickness of the portion of the housing 120 in which each of the power source unit 108 and the control substrate 110 is provided. In addition, in this way, in a case where the thickness of the portion of the housing 120 in which each of the power source unit 108 and the control substrate 110 is provided and the thickness of the portion of the housing 120 in which the radiation detector 10 is provided are made different, and in a case where a step is generated at a boundary part between the two portions, there is a concern that a sense of discomfort may be given to a subject who comes into contact with a boundary part 120B. Therefore, the form of the boundary part 120B is preferably in a state of having an inclination.

Accordingly, it is possible to construct an ultra-thin portable electronic cassette according to the thickness of the radiation detector 10.

Additionally, for example, in this case, the materials of the housing 120 may be different in the portion of the housing 120 in which each of the power source unit 108 and the control substrate 110 is provided and the portion of the housing 120 in which the radiation detector 10 is provided. Moreover, for example, the portion of the housing 120 in which each of the power source unit 108 and the control substrate 110 is provided and the portion of the housing 120 in which the radiation detector 10 is provided may be separated configured.

Figure 8:
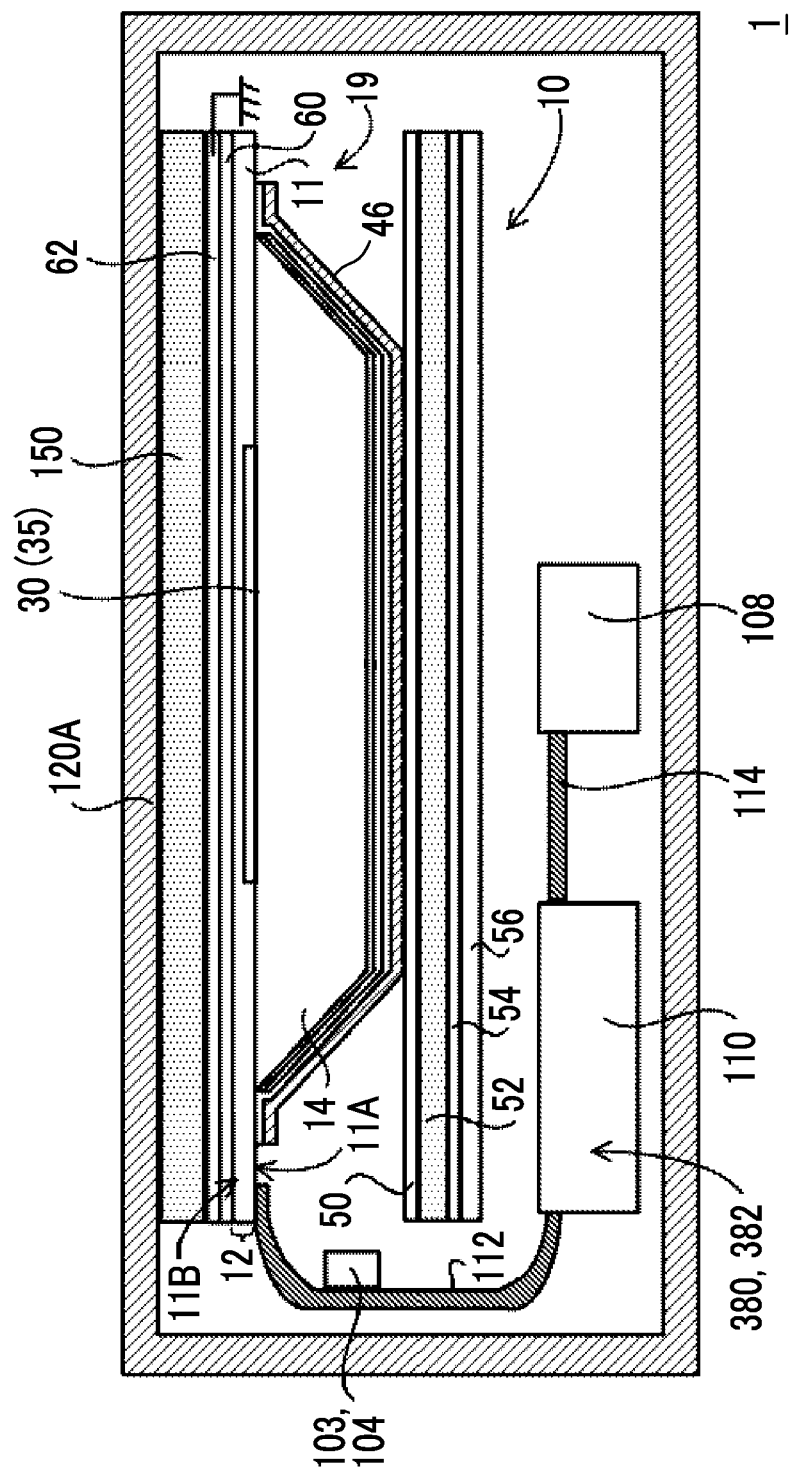
FIG. 8 is a cross-sectional view showing another example of the radiographic imaging apparatus of the embodiment.

Additionally, in the radiographic imaging apparatus 1, as in the example shown in FIG. 8, the radiation detector 10, the control substrate 110, and the power source unit 108 may be housed in the housing 120 in a line in order from the top plate 120A side to which the radiation R is radiated.

As described above, the radiation detector 10 of the present embodiment includes the sensor substrate 12 in which the plurality of pixels 30 for accumulating the electric charge charges generated in response to the light converted from the radiation R are formed in the pixel region 35 of the flexible base material 11, the conversion layer 14 that is provided on the first surface 11A provided with the pixel region 35 of the base material 11 and converts the radiation R into light, the absorption layer 52 that is provided on the side opposite to the side to which the radiation R is radiated in the laminate 19 in which the sensor substrate 12 and the conversion layer 14 are laminated and absorbs the influence of the irregularities generated on the conversion layer 14 on the sensor substrate 12, and the rigid plate 56 that is provided on the side opposite to the side of the absorption layer 52 facing the laminate 19 and has a higher stiffness than the sensor substrate 12.

As described above, according to the radiation detector 10 of the present embodiment, the absorption layer 52 has the shape according to the irregularities generated in the conversion layer 14 of the laminate 19 due to the irregularities of the laminate 19 of the radiation detector 10, the housing 120, or the like. Therefore, the influence of the irregularities on the sensor substrate 12 can be suppressed. Therefore, by suppressing the generation of the irregularities on the sensor substrate 12, according to the radiation detector 10 of the present embodiment, the image unevenness or the like of the radiographic image caused by the irregularities of the sensor substrate 12 can be suppressed, and the quality of the radiographic image can be improved.

Figure 9:
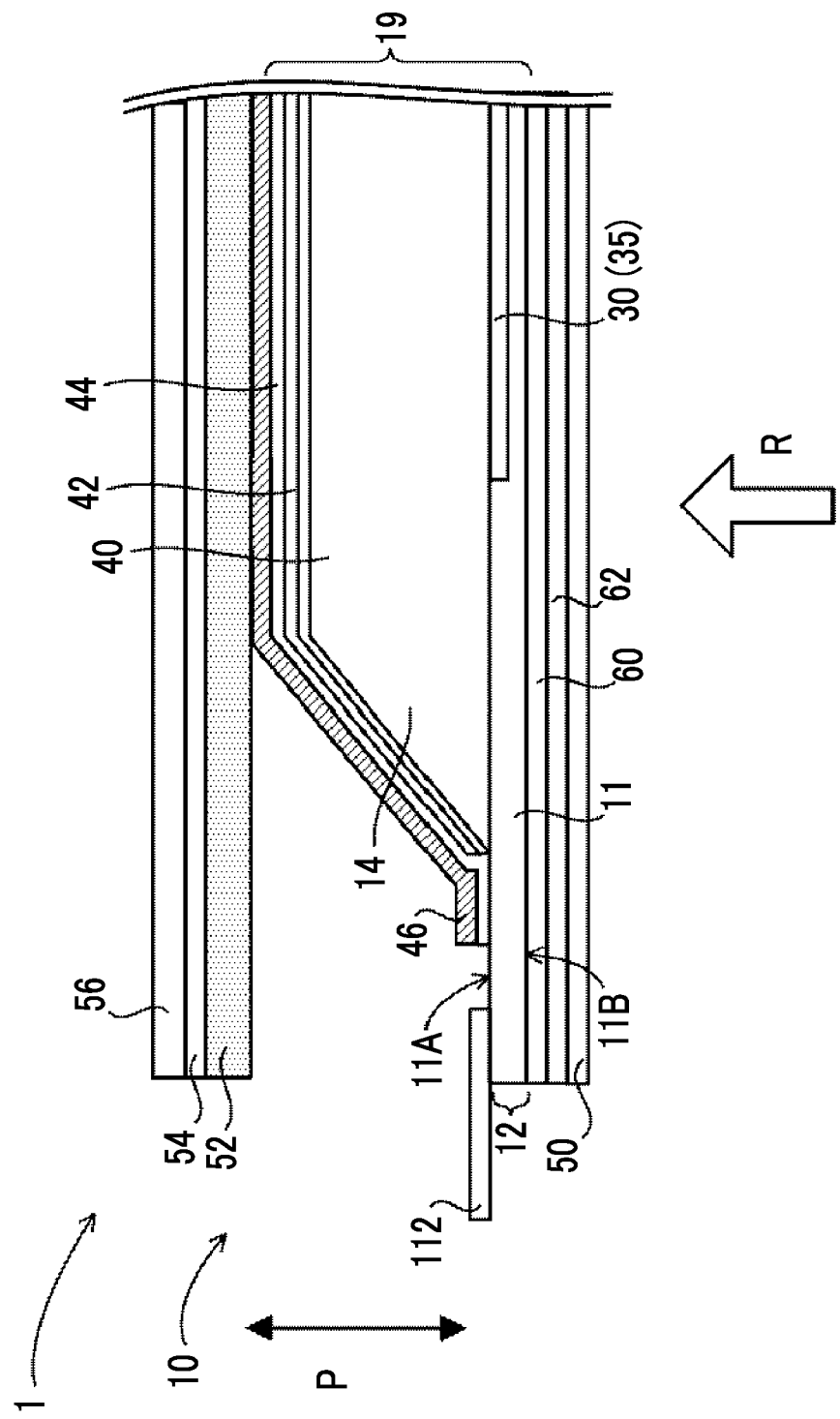
FIG. 9 is a cross-sectional view of another example of the radiation detector of the embodiment.

In addition, the position where the reinforcing substrate 50 is provided is not limited to the position shown in the present embodiment (refer to FIG. 4), and as shown in FIG. 9, the reinforcing substrate 50 may be provided at a position on the opposite side of the laminate 19, specifically, on the side of the antistatic layer 60 and the protective layer 62. In this case, the present invention is not limited to the example shown in FIG. 9, and for example, a form may be adopted in which the reinforcing substrate 50 may be provided between the antistatic layer 60 and the sensor substrate 12.

Additionally, although the ISS type radiation detector 10 (radiographic imaging apparatus 1) has been described above, as shown in FIG. 10, the radiation detector 10 (radiographic imaging apparatus 1) may be a penetration side sampling (PSS) type radiation detector 10 (radiographic imaging apparatus 1) in which the radiation R is radiated from the conversion layer 14 side. Also in the radiation detector 10 shown in FIG. 10, the absorption layer 52 that absorbs the influence of the irregularities generated on the conversion layer 14 on the sensor substrate 12 may be provided on the side opposite to the side on which the radiation R is radiated in the laminate 19 in which the sensor substrate 12 and the conversion layer 14 are laminated. Additionally, the rigid plate 56, which is provided on the side opposite to the side of the absorption layer 52 facing the laminate 19 and has a higher stiffness than the sensor substrate 12, is provided.

Figure 10:
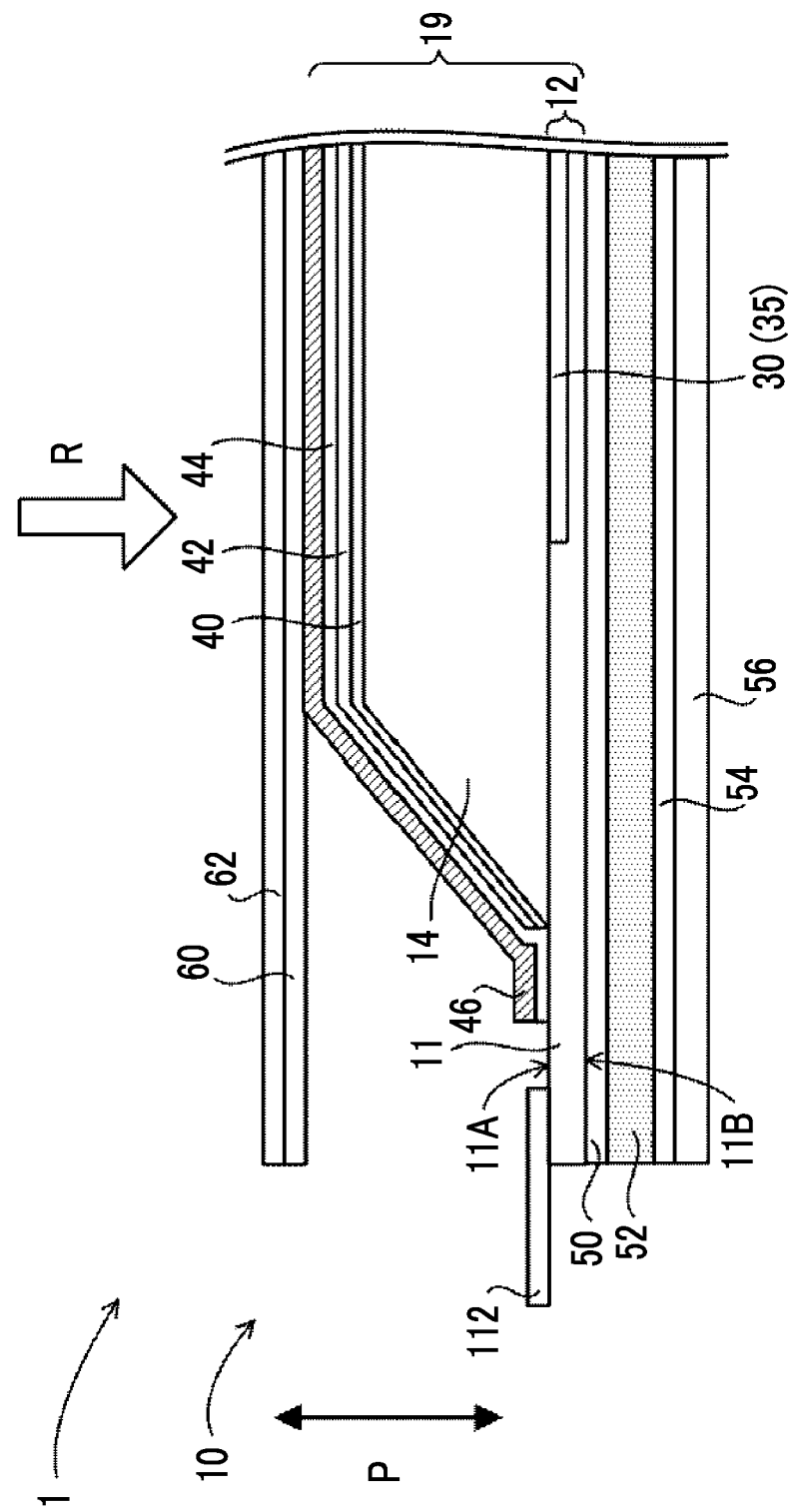
FIG. 10 is a cross-sectional view showing an example of an irradiation side sampling (ISS) type radiation detector of the embodiment.

Also in the radiation detector 10 shown in FIG. 10, the absorption layer 52 has the shape according to the irregularities generated in the conversion layer 14 of the laminate 19 due to the irregularities of the laminate 19 of the radiation detector 10 or the housing 120 and the like. Therefore, the influence of the irregularities on the sensor substrate 12 can be suppressed. Therefore, by suppressing the generation of the irregularities on the sensor substrate 12, according to the radiation detector 10 of the present embodiment, the image unevenness or the like of the radiographic image caused by the irregularities of the sensor substrate 12 can be suppressed, and the quality of the radiographic image can be improved.

Additionally, in the above embodiments, as shown in FIG. 1, an aspect in which the pixels 30 are two-dimensionally arranged on a matrix has been described. However, the invention is not limited to the aspect, and for example, the pixels 30 may be one-dimensionally arranged or may be arranged in a honeycomb shape. Additionally, the shape of the pixels is also not limited, and may be a rectangular shape, or may be a polygonal shape, such as a hexagonal shape. Moreover, the shape of the pixel region 35 is also not limited.

Additionally, the shape or the like of the conversion layer 14 is not limited to the above embodiments. In the above embodiments, an aspect in which the shape of the conversion layer 14 is a rectangular shape similarly to the shape of the pixel region 35 has been described. However, the shape of the conversion layer 14 may not be the same shape as the pixel region 35. Additionally, the shape of the pixel region 35 may not be a rectangular shape but may be, for example, other polygonal shapes or a circular shape.

In addition, in the above embodiments, as an example, a form in which the conversion layer 14 of the radiation detector 10 is the scintillator including CsI has been described. However, the conversion layer 14 may be a scintillator in which GOS ($Gd_2O_2S$:Tb) or the like is dispersed in a binder, such as resin. The conversion layer 14 using GOS is formed, for example, by directly applying the binder having the GOS dispersed therein onto the sensor substrate 12, the peeling layer, and the like and then drying and solidifying the binder. As a method of forming the conversion layer 14, for example, a Giza method of applying an application liquid to a region where the conversion layer 14 is formed while controlling the thickness of an applied film may be adopted. In addition, in this case, surface treatment for activating the surface of the pixel region 35 may be performed before the binder having the GOS dispersed therein is applied. Additionally, an interlayer insulating film may be provided as a surface protective film on the surface of the pixel region 35.

In addition, it goes without saying that the configurations of the radiographic imaging apparatuses 1 and the radiation detectors 10 that are described in the above embodiments are merely examples, and can be changed in response to situations without departing from the scope of the present invention.

The disclosure of Japanese Patent Application No. 2019-086596 filed on Apr. 26, 2019 is incorporated in the present specification by reference in its entirety.

All documents, patent applications, and technical standards described in the present specification are incorporated in the present specification by reference in their entireties to the same extent as in a case where the individual documents, patent applications, and technical standards are specifically and individually written to be incorporated by reference.

What is claimed is:

1. A radiographic imaging apparatus comprising:
a radiation detector comprising:
a sensor substrate in which a plurality of pixels for accumulating electric charges generated in response to light converted from radiation is formed in a pixel region of a flexible base material;
a conversion layer that is provided on a surface of the base material provided with the pixel region and converts the radiation into light;
an absorption layer that is provided on a side opposite to a side to which the radiation is radiated in a laminate in which the sensor substrate and the conversion layer are laminated and absorbs influence of irregularities generated on the conversion layer on the sensor substrate;
a rigid plate that is provided on a side of the absorption layer opposite to a side facing the laminate and has a higher stiffness than the sensor substrate; and
a reinforcing substrate that is provided between the absorption layer and the laminate and that disperses a compressive force applied to the absorption layer in an in-plane direction of the absorption layer; and
a housing in which the radiation detector is housed in order of the laminate, the absorption layer, and the rigid plate from the side to which the radiation is radiated.

2. The radiographic imaging apparatus according to claim 1,
a durometer hardness of the absorption layer is smaller than a durometer hardness of the entire laminate.

3. The radiographic imaging apparatus according to claim 1,
wherein the absorption layer has a surface resistance value of $10^{13}\Omega$ or less.

4. The radiographic imaging apparatus according to claim 1, further comprising:
a reinforcing substrate that is provided on a side of the laminate opposite to the absorption layer side and that disperses a compressive force applied to the absorption layer in an in-plane direction of the absorption layer.

5. The radiographic imaging apparatus according to claim 1, further comprising:
a radiation-shielding layer shielding the radiation and provided between the absorption layer and the rigid plate.

6. The radiographic imaging apparatus according to claim 1,
wherein the rigid plate is a plate having carbon as a material.

7. The radiographic imaging apparatus according to claim 1, further comprising:
a buffer member that is provided on a side of the laminate on which the radiation is incident.

8. The radiation detector according to claim 1, wherein the conversion layer contains columnar crystals of CsI.

9. The radiographic imaging apparatus according to claim 1, further comprising:
- a control unit that outputs a control signal for reading out the electric charges accumulated in the plurality of pixels;
- a drive unit that reads out the electric charges from the plurality of pixels in accordance with the control signal; and
- a signal processing unit that receives electrical signals according to the electric charges read from the plurality of pixels and generates image data according to the received electrical signals to output the image data to the control unit.

10. The radiographic imaging apparatus according to claim 1, wherein the reinforcing substrate has a bending elastic modulus of 150 MPa or more and 2,500 MPa or less.

11. The radiographic imaging apparatus according to claim 1, wherein the reinforcing substrate has a bending stiffness of 540 $Pacm^4$ or more and 140,000 $Pacm^4$ or less.

* * * * *